United States Patent [19]

Shimada et al.

[11] Patent Number: 5,382,692

[45] Date of Patent: Jan. 17, 1995

[54] ELECTROPHOTOGRAPHIC PHOTOCONDUCTORS AND TERTIARY AMINE COMPOUNDS HAVING CONDENSED POLYCYCLIC GROUP FOR USE IN THE SAME

[75] Inventors: Tomoyuki Shimada, Numazu; Masaomi Sasaki, Susono; Tamotsu Aruga, Mishima, all of Japan

[73] Assignee: Ricoh Company, Ltd., Tokyo, Japan

[21] Appl. No.: 15,339

[22] Filed: Feb. 9, 1993

Related U.S. Application Data

[62] Division of Ser. No. 490,468, Mar. 8, 1990, Pat. No. 5,219,692.

[30] Foreign Application Priority Data

| Mar. 29, 1989 | [JP] | Japan | 1-077839 |
| Jun. 14, 1989 | [JP] | Japan | 1-151605 |
| Jul. 25, 1989 | [JP] | Japan | 1-191640 |

[51] Int. Cl.⁶ .............. C07C 211/55; C07C 211/58; C07C 211/61; G03G 15/044
[52] U.S. Cl. .................. 564/426; 564/427; 564/429; 430/59
[58] Field of Search ............ 564/426, 427, 429; 430/59

[56] References Cited

U.S. PATENT DOCUMENTS

| 4,450,218 | 5/1984 | Takei et al. | 430/59 |
| 4,540,651 | 9/1985 | Fujimaki et al. | 430/59 |

*Primary Examiner*—Richard L. Raymond
*Assistant Examiner*—Mary C. Cebilak
*Attorney, Agent, or Firm*—Oblon, Spivak, McClelland, Maier, & Neustadt

[57] ABSTRACT

An electrophotographic photoconductor comprising an electroconductive support, and a photoconductive layer formed thereon comprising at least one tertiary amine compound having a condensed polycyclic hydrocarbon group of formula (I):

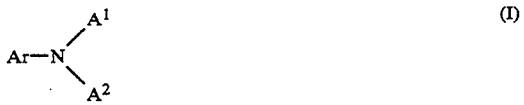

wherein $A^1$ and $A^2$ each independently represent an unsubstituted or substituted alkyl group or aryl group, and Ar represents an unsubstituted or substituted condensed polycyclic hydrocarbon group. Furthermore, novel tertiary amine compounds having a condensed polycyclic hydrocarbon group are disclosed.

5 Claims, 8 Drawing Sheets

ELECTROPHOTOGRAPHIC PHOTOCONDUCTORS AND TERTIARY AMINE COMPOUNDS HAVING CONDENSED POLYCYCLIC GROUP FOR USE IN THE SAME

This is a divisional application of copending application Ser. No. 07/490,468, filed on Mar. 8, 1990, now U.S. Pat. No. 5,219,692.

BACKGROUND OF THE INVENTION

1. Field of the Invention

This invention relates to electrophotographic photoconductors, and more particularly to electrophotographic photoconductor whose photoconductive layer comprises at least one tertiary amine compound having a condensed polycyclic hydrocarbon group, and to tertiary amine compounds having a polycyclic hydrocarbon group which can be used as photoconductive materials in the photoconductors.

2. Discussion of Background

Conventionally, inorganic materials such as selenium, cadmium sulfide and zinc oxide are used as photoconductive materials of an electrophotographic photoconductor in the electrophotographic process. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electrical charge of the exposed areas, so that a latent electrostatic image is formed on the photoconductor. The thus formed latent electrostatic image is developed by a developer comprising a coloring agent such as a dye and a pigment, and a binder agent such as a polymeric material, to a visible image.

Fundamental characteristics required for the photoconductor in such an electrophotographic process are:
(1) chargeability to an appropriate potential in the dark,
(2) minimum dissipation of electrical charge in the dark, and
(3) rapid dissipation of electrical charge when exposed to the light.

However, while the above-mentioned inorganic materials have many advantages, they have several shortcomings form the viewpoint of practical use.

For instance, a selenium photoconductor, which is widely used at present, completely satisfies the above-mentioned requirements (1) to (3), but it has the shortcomings that its manufacturing conditions are difficult to control, and accordingly its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be easily obtained by coating a dispersion of cadmium sulfide particles and zinc oxide particles in a binder resin on a support. However, they are poor in mechanical properties, such as surface smoothness, hardness, tensile strength and wear resistance. Therefore, they cannot be used in the repeated operation, as they are.

To solve the above-mentioned problems of the inorganic materials, various electrophotographic photoconductors employing organic materials are proposed recently and some are put to practical use. For example, there are known a photoconductor comprising poly-N-vinylcarbazole and 2,4,7-trinitrofluorene-9-on, as disclosed in U.S. Pat. No. 3,484,237; a photoconductor prepared by sensitizing poly-N-vinylcarbazole with a pigment of pyrylium salt, as disclosed in Japanese Patent Publication 48-25658; a photo-conductor comprising as the main component an organic pigment, as disclosed in Japanese Laid-Open Patent Application 47-37543; a photoconductor comprising as the main component an eutectic crystal complex of a dye and a resin, as disclosed in Japanese Laid-Open Patent Application 47-10735; a photoconductor prepared by sensitizing a triphenylamine compound with a sensitizer pigment, as disclosed in U.S. Pat. 3,180,730; a photoconductor comprising an amine derivative as a charge transporting material as disclosed in Japanese Laid-Open Patent Application 57-195254, a photoconductor comprising poly-N-vinylcarbazole and an amine derivative as a charge transporting material, as disclosed in Japanese Laid-Open Patent Application 58-1155, and photoconductors comprising as a photoconductive material a polyfunctional tertiary amine compound, especially a benzidine compound, as disclosed in U.S. Pat. 3,265,496, Japanese Patent Publication 39-11546 and Japanese Laid-Open Patent Application 53-27033.

Although the above photoconductors have excellent characteristics, and can be put in practical use, they are still unsatisfactory as photoconductors for use in electrophotography.

SUMMARY OF THE INVENTION

It is therefore a first object of the present invention to provide an electrophotographic photoconductor having good durability, free from the conventional shortcomings, which can completely satisfy all the requirements in the electrophotographic process, and can be easily manufactured at relatively low cost.

A second object of the present invention is to provide a charge transporting material for use in the above-mentioned electrophotographic photoconductor.

A third object of the present invention is to provide novel tertiary amine compounds having a condensed polycyclic hydrocarbon group used as photoconductive materials in the electrophotographic photoconductor.

The first object of the present invention can be achieved by an electrophotographic photoconductor comprising an electroconductive support and a photoconductive layer formed thereon comprising at least one tertiary amine compound having a condensed polycyclic hydrocarbon group, represented by formula (I):

in which $A^1$ and $A^2$ each independently represent an unsubstituted or substituted alkyl or aryl group, and Ar represents an unsubstituted or substituted condensed polycyclic hydrocarbon group.

The second object of the present invention can be attained by a charge transporting material for use in the electrophotographic photoconductor, which comprises a tertiary amine compound having the above-mentioned formula (I).

The third object of the present invention can be attained by tertiary amine compounds having formula (II):

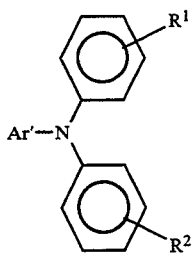

wherein Ar' represents a condensed polycyclic hydrocarbon group having 18 or less carbon atoms, $R^1$ and $R^2$ each independently represent hydrogen, an unsubstituted or substituted alkyl group, an unsubstituted or substituted alkoxyl group, or an unsubstituted or substituted phenyl group.

BRIEF DESCRIPTION OF THE DRAWINGS

A more complete appreciation of the invention and many of the attendant advantageous thereof will be readily obtained as the same become better understood by reference to the following detailed description when considered in connection with the accompanying drawings, wherein.

DETAILED DESCRIPTION OF THE PREFERRED EMBODIMENTS

Figure 1:
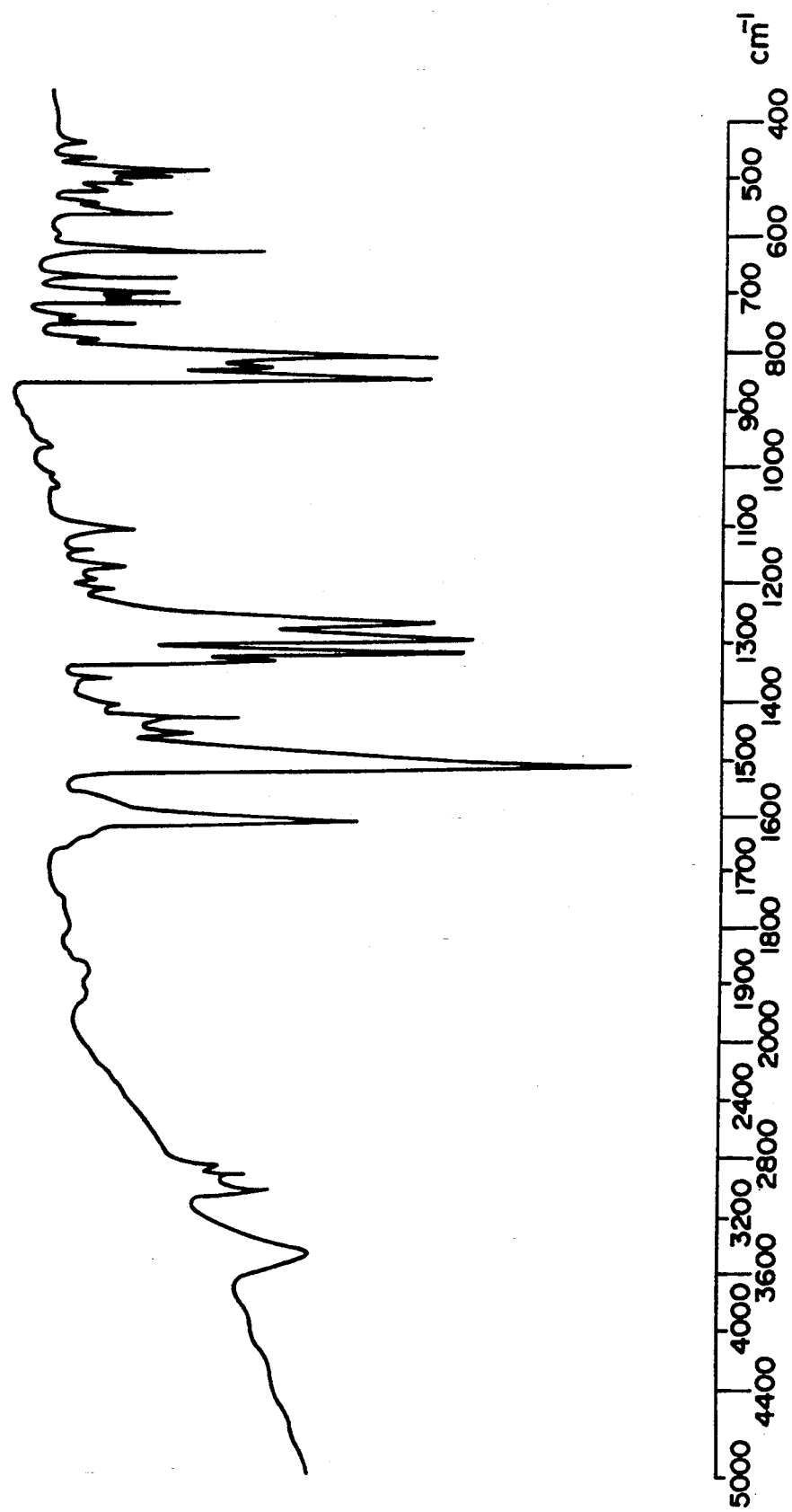
FIG. 1 is a chart of an infrared absorption spectrum, taken by the KBr tablet method, of the tertiary amine compound having a condensed polycyclic group according to the present invention prepared in Synthesis Example 1.

According to the present invention, an electrophotographic photoconductor comprising an electroconductive support and a photoconductive layer formed thereon, which photoconductive layer comprises at least one tertiary amine compound having a condensed polycyclic hydrocarbon group represented by the following formula (I) is provided:

in which $A^1$ and $A^2$ each independently represent an unsubstituted or substituted alkyl or aryl group, and Ar represents an unsubstituted or substituted condensed polycyclic hydrocarbon group.

A more specific explanation of the tertiary amine compound, represented by formula (I), is given below.

A preferred condensed polycyclic hydrocarbon group represented by Ar in formula (I) is a group having a ring consisting of 18 or less carbon atoms; for instance, a pentalenyl group, an indenyl group, a naphthyl group, an azulenyl group, a heptalenyl group, a biphenylenyl group, an as-indacenyl group, a fluorenyl group, an s-indacenyl group, an acenaphthylenyl group, a pleiadenyl group, an acenaphthenyl group, a phenalenyl group, a phenanthryl group, an anthryl group, a fluoranthenyl group, an acephenanthrylenyl group, an aceanthrylenyl group, a triphenylenyl group, a pyrenyl group, a chrysenyl group and a naphthacenyl group.

Ar may have any of the following groups as a substituent.

(1) A halogen, a cyano group, and a nitro group.

(2) A linear or branched alkyl group having 1 to 12 carbon atoms, preferably 1 to 8 carbon atoms, and more preferably 1 to 4 carbon atoms. The alkyl group may have as a substituent fluorine, a hydroxyl group, a cyano group, an alkoxyl group having 1 to 4 carbon atoms, or a phenyl group which may have a substituent such as a halogen, an alkyl group having 1 to 4 carbon atoms, or an alkoxyl group having 1 to 4 carbon atoms.

Specific examples of the alkyl group include a methyl group, an ethyl group, a n-propyl group, an i-propyl group, a t-butyl group, a s-butyl group, a n-buryl group, an i-butyl group, a trifluoromethyl group, a 2-hydroxyethyl group, a 2-cyanoethyl group, a 2-ethoxyethyl group, a 2-methoxyethyl group, a benzyl group, a 4-chlorobenzyl group, a 4-methylbenzyl group, a 4-ethoxybenzyl group and a 4-phenylbenzyl group.

(3) An alkoxyl group represented by —$OR^1$.
$R^1$ represents an alkyl group defined in the above item (2).

Specific examples of the alkoxyl group include a methoxy group, an ethoxy group, a n-propoxy group, an i-propoxy group, a t-butoxy group, a n-butoxy group, a s-butoxy group, an i-butoxy group, a 2-hydroxyethoxy group, a2-cyanoethoxy group, a benzyloxy group, a 4-methylbenzyloxy group and a trifluoromethoxy group.

(4) An aryloxy group.

An aryl group in the aryloxy group is a phenyl group or a naphthyl group. The aryl group may have as a substituent an alkoxyl group having 1 to 4 carbon atoms, an alkyl group having 1 to 4 carbon atoms, or a halogen. Specific examples of the aryloxy group include a phenoxy group, a 1-naphthyloxy group, a 2-naphthyloxy group, a 4-methylphenoxy group, a 4-methoxyphenoxy group, a 4-chlorophenoxy group and a 6-methyl-2-naphthyloxy group.

(5) An alkylmercapto group or a phenylmercapto group represented by —$SR^1$.

$R^1$ represents an alkyl group defined in the above item (2), or a phenyl group which may have a substituent.

Specific examples of the alkylmercapto group and the phenylmercapto group include a methylthio group, an ethylthio group, a phenylthio group and a p-methylphenylthio group. (6) A group represented by

wherein $R^2$ and $R^3$ each independently represent hydrogen, an alkyl group defined in the above item (2), or an aryl group such as a phenyl group, a biphenylyl group or a naphthyl group. The aryl group may have as a substituent an alkoxyl group having 1 to 4 carbon atoms, an alkyl group having 1 to 4 carbon atom, or a halogen. $R^2$ can form a ring along with $R^3$, or $R^2$ and $R^3$ can form a ring along with a carbon atom contained in the aryl group.

Specific examples of the group represented by the above formula include an amino group, a diethylamino group, an N-methyl-N-phenylamino group, an N,N-diphenylamino group, an N,N-di(p-tolyl)amino group, a dibenzylamino group, a piperidino group, a morpholino group and a julolidyl group.

(7) A methylene dioxy group, and an alkylene dioxy group or an alkylene dithio group such as a methylene dithio group.

The aryl group represented by $A^1$ or $A^2$ in formula (I) may be a carbocyclic aromatic group or a heterocyclic aromatic group.

Examples of the carbocyclic aromatic group include non-condensed carbocyclic aromatic groups such as a phenyl group, a biphenylyl group and a terphenyl group, and condensed polycyclic hydrocarbon groups.

Examples of the condensed polycyclic hydrocarbon groups are the same as those represented by Ar defined before.

These aryl groups may have as a substituent any of the groups described in the above items (1) through (7).

Examples of the heterocyclic aromatic groups include a pyridyl group, a pyrimidyl group, a pyrazinyl group, a triazinyl group, a furanyl group, a pyrrolyl group, a thiophenyl group, a quinolyl group, a coumarinyl group, a benzofuranyl group, a benzimidazolyl group, a benzoxazolyl group, a dibenzofuranyl group, a benzothiophenyl group, a dibenzothiophenyl group, an indolyl group, a carbazolyl group, a pyrazolyl group, an imidazolyl group, an oxazolyl group, an isooxazolyl group, a thiazolyl group, an indazolyl group, a benzothiazolyl group, a pyridazinyl group, a cinnolyl group, a quinazolyl group, a quinoxalyl group, a phthalazinyl group, a phthalazinedionyl group, a phthalamidyl group, a chromonyl group, a naphtholactamyl group, a quinolonyl group, an o-sulfobenzoic acid imidyl group, a maleic acid imidyl group, a naphthalidinyl group, a benzimidazonyl group, a benzoxazonyl group, a benzothiazolonyl group, a benzothiazothionyl group, a quinazolonyl group, a quinoxalonyl group, a phthalazonyl group, a dioxopyrimidinyl group, a pyridonyl group, an isoquinolonyl group, an isoquinolinyl group, an isothiazolyl group, a benzisooxazolyl group, a benzisothiazolyl group, an indazolonyl group, an acridinyl group, an acridonyl group, a quinazolienedionyl group, a quinoxalinedionyl group, a benzoxadine dionyl group, a benzoxadinolyl group and naphthalimidyl group.

The substituted or unsubstituted alkyl group represented by $A^1$ or $A^2$ in formula (I) is the same as those defined in the above item (2).

The tertiary amine compounds having a condensed polycyclic hydrocarbon group of formula (I) can be prepared by reacting a condensed polycyclic hydrocarbon compound substituted with an amino group, represented by formula (III):

wherein Ar represents an unsubstituted or substituted condensed polycyclic hydrocarbon group, with a halogenated compound represented by formula (IV):

wherein A represents a substituted or unsubstituted alkyl or aryl group, and X represents a halogen, or reacting a condensed polycyclic hydrocarbon compound substituted with a halogen, represented by formula (V):

wherein Ar is the same as defined above, and X represents a halogen, with an amino compound represented by formula (VI)

wherein $A^1$ and $A^2$ each independently represent a substituted or unsubstituted alkyl or aryl group.

Representative examples of the tertiary amine compounds having the condensed polycyclic hydrocarbon group for use in electrophotographic photoconductors according to the present invention are shown in Table 1.

TABLE 1

| Compound No. | Formula | Melting Point (°C.) |
|---|---|---|
| (1) | H₃C — [structure] — CH₃ | 181.0–181.5 |

TABLE 1-continued

| Compound No. | Formula | Melting Point (°C.) |
|---|---|---|
| (2) | [structure] | 136.5–137.5 |
| (3) | [structure] | 214.0–215.0 |
| (4) | [structure] | 167.0–168.0 |
| (5) | [structure] | 239.0–240.0 |
| (6) | [structure] | 173.0–174.0 |
| (7) | [structure] | 173.0–174.0 |
| (8) | [structure] | 127.0–128.0 |
| (9) | [structure] | oily material |
| (10) | [structure] | 139.0–140.0 |
| (11) | [structure] | 94.0–95.5 |
| (12) | [structure] | 137.0–138.0 |
| (13) | [structure] | 225.5–226.0 |
| (14) | [structure] | 150.5–151.5 |
| (15) | [structure] | 130.5–131.5 |
| (16) | [structure] | 196.5–197.5 |
| (17) | [structure] | 155.5–156.5 |

In particular, among the tertiary amine compounds having a condensed polycyclic group represented by formula (I), those compounds having Ar which represents a condensed polycyclic hydrocarbon group having 18 or less carbon atoms, $A^1$ and $A^2$ which independently represent an aryl group having as a substituent hydrogen, a substituted or unsubstituted alkyl group, a substituted or unsubstituted alkoxyl group, or a substituted or unsubstituted phenyl group are novel. Namely, such novel compounds are represented by the following formula (II):

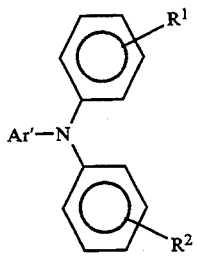

(II)

wherein Ar' represents a condensed polycyclic group having 18 or less carbon atoms, $R^1$ and $R^2$ each independently represent hydrogen, a substituted or unsubstituted alkyl group, a substituted or unsubstituted alkoxyl group, or a substituted or unsubstituted phenyl group.

Specific examples of Ar' in formula (II) include a naphthyl group, a fluorenyl group, an acenaphthenyl group, an anthryl group, a pyrenyl group, a phenanthryl group, a chrysenyl group and a fluoranthenyl group.

Specific examples of the alkyl group represented by $R^1$ or $R^2$ include an alkyl group having 1 to 6 carbon atoms, such as a methyl group, an ethyl group, a propyl group and a butyl group.

Specific examples of the alkoxyl group represented by $R^1$ or $R^2$ include an alkoxyl group having 1 to 6 carbon atoms such as a methoxy group, an ethoxy group and a propoxy group.

The alkyl group represented by $R^1$ or $R^2$ may have as a substituent a phenyl group, a halogen, an alkoxyl group or an aryloxy group.

The phenyl group represented by $R^1$ or $R^2$ may have as a substituent an alkyl group having 1 to 6 carbon atoms, such as a methyl group, an ethyl group, a propyl group or a butyl group, an alkoxyl group having 1 to 6 carbon atoms such as a methoxy group, an ethoxy group or a propoxy group, or a halogen such as bromine or chlorine.

The tertiary amine compound having a condensed polycyclic group, represented by formula (II), can be prepared by reacting an amino condensed polycyclic hydrocarbon derivative represented by formula (III'):

 (III')

wherein Ar' is the same as defined above, with a halobenzene derivative represented by formula (III'):

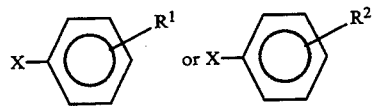

(IV')

wherein $R^1$ and $R^2$ are the same as defined above, and X represents a halogen, or by reacting a halocondensed polycyclic hydrocarbon derivative represented by formula (V'):

 (V')

wherein Ar' and X are the same as defined above, with a diphenyl amine derivative represented by formula (V'):

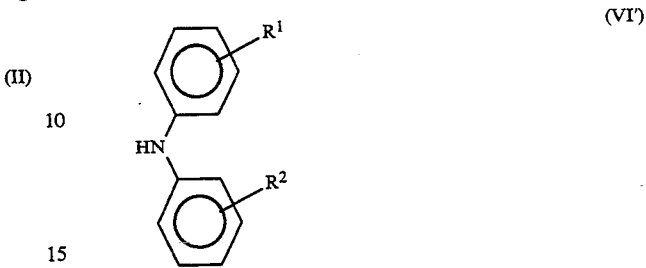

(VI')

wherein $R^1$ and $R^2$ are the same as defined above.

In the above reaction, copper powder, copper oxide or halogenated copper which serves as a catalyst, and an alkaline material or an alkali salt are added to the reaction system. The amount of the alkaline material or the alkali salt is such that the hydrogen halogenide produced during the condensation reaction can be completely neutralized.

The reaction proceeds in the presence or absence of a solvent under a nitrogen atmosphere. The reaction temperature is approximately 150° to 250° C.

Examples of the alkaline material added to the reaction system include sodium hydroxide, and potassium hydroxide, and examples of the alkali salt include sodium carbonate and potassium carbonate.

Examples of the solvent usable for the above reaction include nitrobenzene, dichlorobenzene, quinoline, N,N-dimethylformamide, dimethylsulfoxide, N-methyl pyrrolidone and 1,3-dimethyl-2-imidazolidinon.

The above-mentioned tertiary amine compounds having condensed polycyclic group for use in the present invention, which are remarkably effective as photoconductive materials in the electrophotographic photoconductor, are optically or chemically sensitized with a sensitizer such as a dye or Lewis acid. In addition, the tertiary amine compounds effectively function as charge transporting materials in a function-separating type electrophotographic photoconductor where an organic or inorganic pigment serves as a charge generating material.

In the photoconductors according to the present invention, at least one tertiary amine compound of formula (I) is contained in the photoconductive layers 2, 2a, 2b, 2c, 2d and 2e. The tertiary amine compounds can be employed in different ways, for example, as shown in FIGS. 8 through 13.

Figure 8:
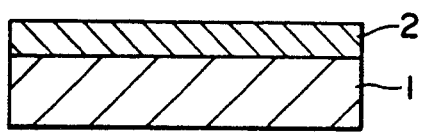
FIG. 8 is a schematic cross-sectional view of an electrophotographic photoconductor according to the present invention.

In the photoconductor as shown in FIG. 8, a photoconductive layer 2 is formed on an electroconductive support 1, which photoconductive layer 2 comprises a tertiary amine compound, a sensitizing dye and a binder agent (binder resin). In this photoconductor, the tertiary amine compound works as a photoconductive material, through which charge carriers necessary for the light decay of the photoconductor are generated and transported. However, the tertiary amine compound itself scarcely absorbs light in the visible light range and, therefore, it is necessary to add a sensitizing dye which absorbs light in the visible light range in order to form latent electrostatic images by use of visible light.

Figure 9:
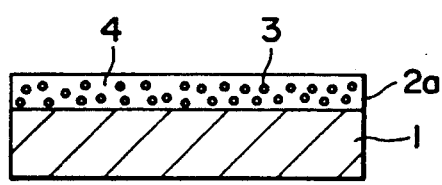

Referring to FIG. 9, there is shown an enlarged cross-sectional view of another embodiment of an electrophotographic photoconductor according to the present invention. In the figure, reference numeral 1 indicates an electroconductive support. On the electroconductive support 1, there is formed a photoconductive layer 2a comprising a charge generating material 3 dispersed in a charge transporting medium 4 comprising a tertiary amine compound and a binder agent. In this embodiment, the tertiary amine compound and the binder agent (or a mixture of the binder agent and a plasticizer) constitute the charge transporting medium 4 in combination. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is basically required that the light-absorption wavelength regions of the charge generating material 3 and the tertiary amine compound do not overlap in the visible light range. This is because, in order that the charge generating material 3 produce charge carriers efficiently, it is necessary that light pass through the charge transporting medium 4 and reach the surface of the charge generating material 3. Since the tertiary amine compounds of the previously described formula (I) do not substantially absorb light in the visible range, they can work effectively as charge transporting materials in combination with the charge generating material 3 which absorbs the light in the visible region and generates charge carriers.

Figure 10:
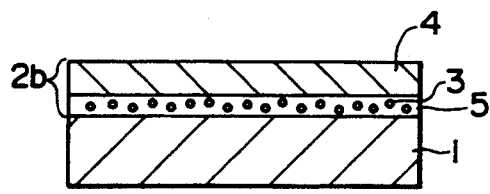

Referring to FIG. 10, there is shown an enlarged cross-sectional view of a further embodiment of an electrophotographic photoconductor according to the present invention. In the figure, there is formed on an electroconductive support 1 a two-layered photoconductive layer 2b comprising a charge generation layer 5 containing a charge generating material 3, and a charge transport layer 4 containing a tertiary amine compound of the previously described formula (I).

In this photoconductor, light which has passed through the charge transport layer 4 reaches the charge generation layer 5, and charge carriers are generated within the charge generation layer 5. The charge carriers which are necessary for the light decay for latent electrostatic image formation are generated by the charge generating material 3, accepted and transported by the charge transport layer 4. In the charge transport layer 4, the tertiary amine compound mainly works for transporting charge carriers. The generation and transportation of the charge carriers are performed by the same mechanism as that in the photoconductor shown in FIG. 3.

Figure 11:
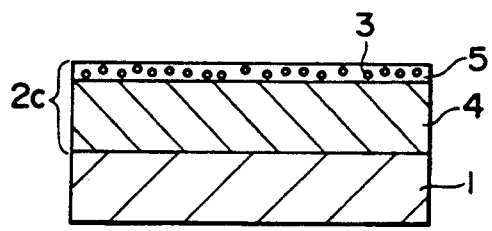
FIGS. 9 through 13 are schematic cross-sectional views of other preferred electrophotographic photoconductors according to the present invention.
Figure 12:
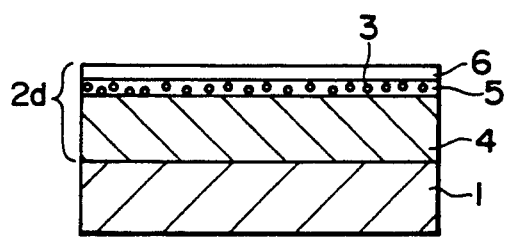

In an electrophotographic photoconductor shown in FIG. 11, a charge generation layer 5 is formed on a charge transport layer 4 containing a tertiary amine compound in a photoconductive layer 2c, thus the overlaying order of the charge generation layer 5 and the charge transport layer 4 is reversed as compared with the electrophotographic photoconductor as shown in FIG. 10. The mechanism of the generation and transportation of charge carriers is substantially the same as that of the photoconductor shown in FIG. 10.

in the above photoconductor, a protective layer 6 may be formed on the charge generation layer 5 as shown in FIG. 12 for protecting the charge generation layer 5.

when the electrophotographic photoconductor according to the present invention as shown in FIG. 8 is prepared, at least one tertiary amine compound of the previously described formula (I) is dispersed in a binder resin solution, and a sensitizing dye is then added to the mixture, so that a photoconductive layer coating liquid is prepared. The thus prepared photoconductive layer coating liquid is coated on an electroconductive support 1 and dried, so that a photoconductive layer 2 is formed on the electroconductive support 1.

it is preferable that the thickness of the photoconductive layer 2 be in the range of 3 to 50 μm, more preferably in the range of 5 to 20 μm. It is preferable that the amount of the tertiary amine compound contained in the photoconductive layer 2 be in the range or 30 to 70 wt. %, more preferably about 50 wt. %.

It is preferable that the amount of the sensitizing dye contained in the photoconductive layer 2 be in the range of 0.1 to 5 wt. %, more preferably in the range of 0.5 to 3 wt. %.

Specific examples of the sensitizing dye for use in the present invention include triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; and pyrylium dyes such as 2,6-diphenyl-4-(N,N-dimethylaminophenyl)thiapyrylium perchlorate and benzopyrylium salts disclosed in Japanese Patent Publication 48-25658.

These sensitizing dyes may be used either alone or in combination.

The electrophotographic photoconductor shown in FIG. 9 can be obtained by dispersing finely-divided particles of the charge generating material 3 in a solution in which at least one tertiary amine compound for use in the present invention and the binder agent are dissolved, coating the above-prepared dispersion on the electroconductive support 1 and then drying the same to form the photoconductive layer 2a.

it is preferable that the thickness of the photoconductive layer 2a be in the range of 3 to 50 μm, more preferably in the range of 5 to 20 μm. It is preferable that the amount of the tertiary amine compound contained in the photoconductive layer 2a be in the range of 10 to 95 wt. %, more preferably in the range of 30 to 90 wt. %.

it is preferable that the amount of the charge generating material 3 contained in the photoconductive layer 2a be in the range of 0.1 to 50 wt. %, more preferably in the range of 1 to 20 wt. %.

Specific examples of the charge generating material 3 for use in the present invention include inorganic pigments such as selenium, selenium-tellurium, cadmium sulfide, cadmium sulfide-selenium and α-silicon; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R (both made by Bayer Co., Ltd.). These charge generating materials may be used either alone or in combination.

The electrophotographic photoconductor shown in FIG. 10 can be obtained as follows:

The charge generating material is vacuum-deposited on the electroconductive support 1, or the dispersion in which finely-divided particles of the charge generating material 3 are dispersed in an appropriate solvent, if necessary, together with the binder agent is coated on the electroconductive support 1 and dried, so that the charge generation layer 5 is formed. When necessary, the charge generation layer 5 is subjected to buffing to adjust the thickness thereof. On the thus formed charge generation layer 5, the coating solution in which at least one tertiary amine compound and the binder agent are dissolved is coated and dried, so that the charge transport layer 4 is formed. In the charge generation layer 5, the same charge generating material as employed in the above-mentioned photoconductive layer 2a can be used.

The thickness of the charge generation layer 5 is 5 μm or less, more preferably 2 μm or less. It is preferable that the thickness of the charge transport layer 4 be in the range of 3 to 50 μm, more preferably in the range of 5 to 20 μm. When the charge generation layer 5 is obtained by coating the dispersion in which finely-divided particles of the charge generating material 3 are dispersed in an appropriate solvent together with the binder agent, it is preferable that the amount of finely-divided particles of the charge generating material 3 contained in the charge generation layer 5 be in the range of 10 to 95 wt. %, more preferably in the range of about 50 to 90 wt. %. It is preferable that the amount of the tertiary amine compound contained in the charge transport layer 4 be in the range of 10 to 95 wt. %, more preferably in the range of 30 to 90 wt. %.

The electrophotographic photoconductor shown in FIG. 11 can be obtained as follows:

The coating solution in which the tertiary amine compound and the binder agent are dissolved is coated on the electroconductive support 1 and dried to form the charge transport layer 4. On the thus formed charge transport layer 4, the dispersion prepared by dispersing finely-divided particles of the charge generating material 3 in the solvent, in which the binder agent is dissolved when necessary, is coated by spray coating and dried to form the charge generation layer 5 on the charge transport layer 4. The amount ratio of the components contained in the charge generation layer and charge transport layer is the same as previously described in FIG. 4.

Figure 5:
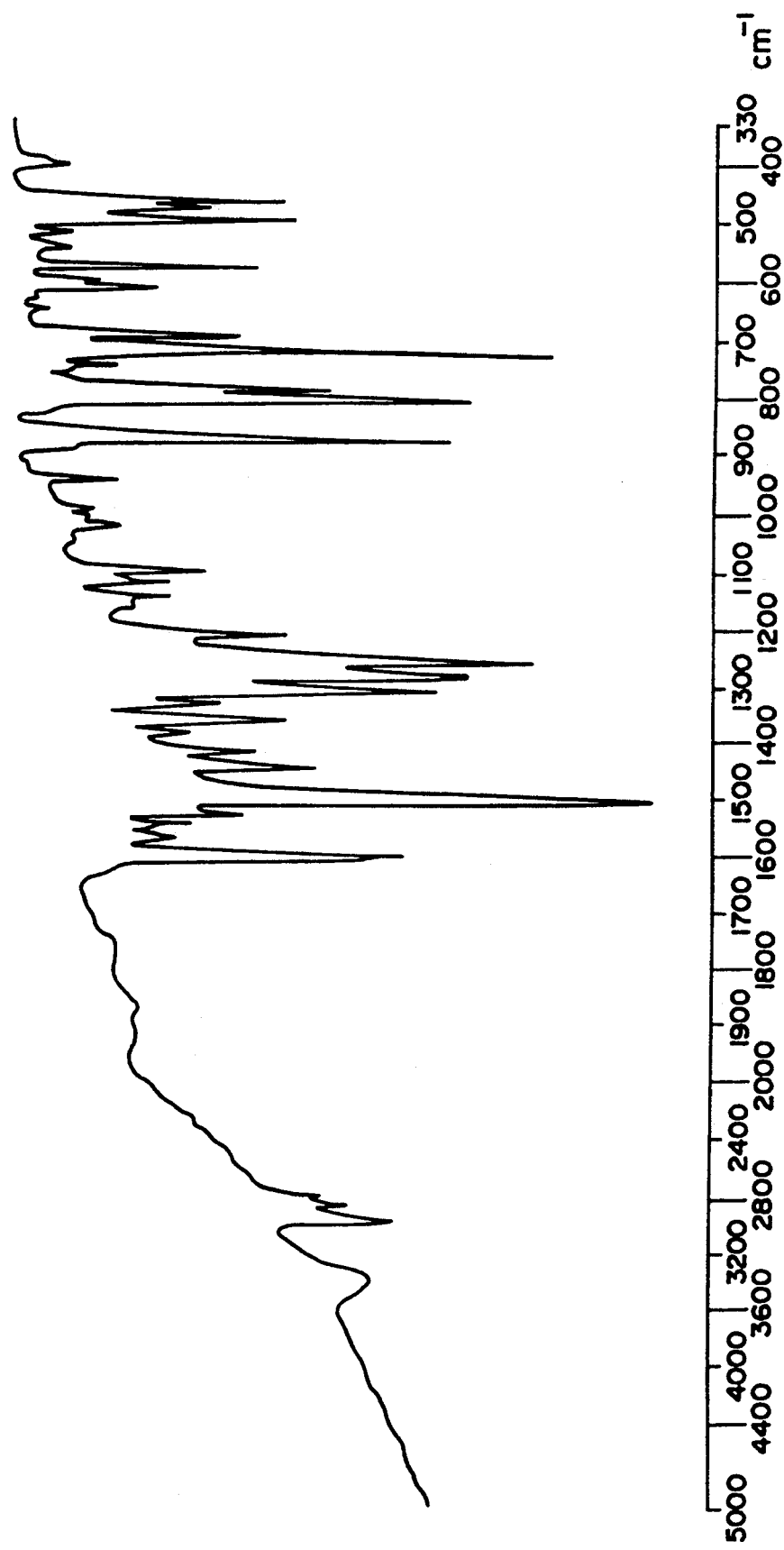
FIG. 5 is a chart of an infrared absorption spectrum, taken by the KBr tablet method, of the tertiary amine compound having a condensed polycyclic group according to the present invention prepared in Synthesis Example 9.

The electrophotographic photoconductor shown in FIG. 12 can be obtained by forming a protective layer 6 on the charge generation layer 5 as obtained in FIG. 5 by spray-coating of an appropriate resin solution. As the resins employed in the protective layer 6, the binder agents wich will be described later can be used.

Figure 13:
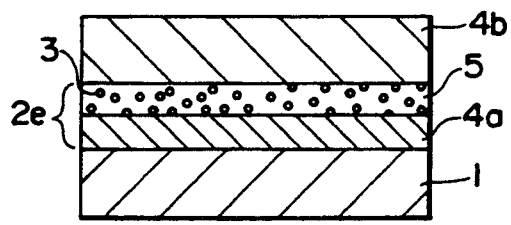

An electrophotographic photoconductor with a structure as shown in FIG. 13 may also be employed in the present invention, which can be obtained by forming a charge transport layer 4a, a charge generation layer 5, and a charge transport layer 4b (which layers may be collectively referred to as a photoconductive layer 2e) successively in that order on an electroconductive support 1, in which either the charge transport layer 4a or the charge transport layer 4b comprises at least one tertiary amine compound and the other charge transport layer comprises a Lewis acid type charge transporting material, for example, fluorenone compounds such as trichlorofluorenone and quinone derivatives.

Specific examples of the electroconductive support for the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, polyketone and polycarbonate; and vinyl copolymers such as polyvinylketone, polystyrene, poly-N-vinylcarbazole and polyacrylamide. All the resins having insulating properties and adhesive force can be employed. Some plasticizers may be added to the above-mentioned binder agent, when necessary. Examples of the plasticizer for use in the present invention are halogenated paraffin, polybiphenyl chloride, dimethylnaphthalene and dibutyl phthalate.

Furthermore, in the electrophotographic photoconductors according to the present invention, an adhesive layer or barrier layer may be interposed between the electroconductive support and the photoconductive layer when necessary. Examples of the material for use in the adhesive layer or barrier layer are polyamide, nitrocellulose and aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and when necessary, the developed image can be transferred to a sheet of paper. The electrophotographic photoconductors according to the present invention have high photosensitivity and improved flexibility.

Other features of this invention will become apparent in the course of the following description of exemplary embodiments, which are given for illustration of the invention and are not intended to be limiting thereof.

Synthesis Example 1

[Synthesis of Tertiary Amine Compound No. 1 in Table 1]

While conducting azeotropical dehydration in a stream of nitrogen using an ester tube, a mixture of 2.17 g (0.01 mol) of 1-aminopyrene, 32.70 g (0.15 mol) of 4-iodinetoluene, 5.53 g (0.04 mol) of potassium carbonate and 0.32 g of copper powder was stirred at a temperature between 206° C. and 209° C. for 6 hours.

The resulting mixture was then cooled to room temperature, and filtered using a Celite. Chloroform was added to the filtrate, and the resulting mixture was washed with water using a separatory funnel, and then dried using magnesium sulfide. The dried mixture was condensed under reduced pressure to obtain an oily product reddish black in color.

The oily product was placed on a silica gel column and eluted with a 1:3 mixed solvent of toluene and n-hexane. The eluate was recrystallized from a mixed solvent of ethanol and ethylacetate, thereby obtaining 1.65 g of the captioned compound, 1-N,N-bis(4-methylphenyl)amino pyrene, as light yellow leaf-shaped crystals.

Yield: 41.6% Melting Point: 181.0°–181.5° C.

| Elementary Analysis: (for $C_{30}H_{23}N$) | | | |
| --- | --- | --- | --- |
| | % C | % H | % N |
| Found: | 90.64 | 5.61 | 3.68 |
| Calculated: | 90.64 | 5.83 | 3.53 |

FIG. 1 shows an infrared spectrum of tertiary amine compound No. 1, taken by use of a KBr tablet.

Synthesis Example 2

[Synthesis of Tertiary Amine Compound No. 2 in Table 1]

The synthesis procedure in Synthesis Example 1 was applied to obtain tertiary amine compound No. 2 in Table 1.

The melting point of the obtained compound, and the results of elementary analysis are shown in Table 2.

Synthesis Example 3

[Synthesis of Tertiary Amine Compound No. 5 in Table 1]

The synthesis procedure in Synthesis Example 1 was applied to obtain tertiary amine compound No. 5 in Table 1.

The melting point of the obtained compound, and the results of elementary analysis are shown in Table 2.

Synthesis Example 4

[Synthesis of Tertiary Amine Compound No. 6 in Table 1]

The synthesis procedure in Synthesis Example 1 was applied to obtain tertiary amine compound No. 4 in Table 1.

The melting point of the obtained compound, and the results of elementary analysis are shown in Table 2.

Figure 2:
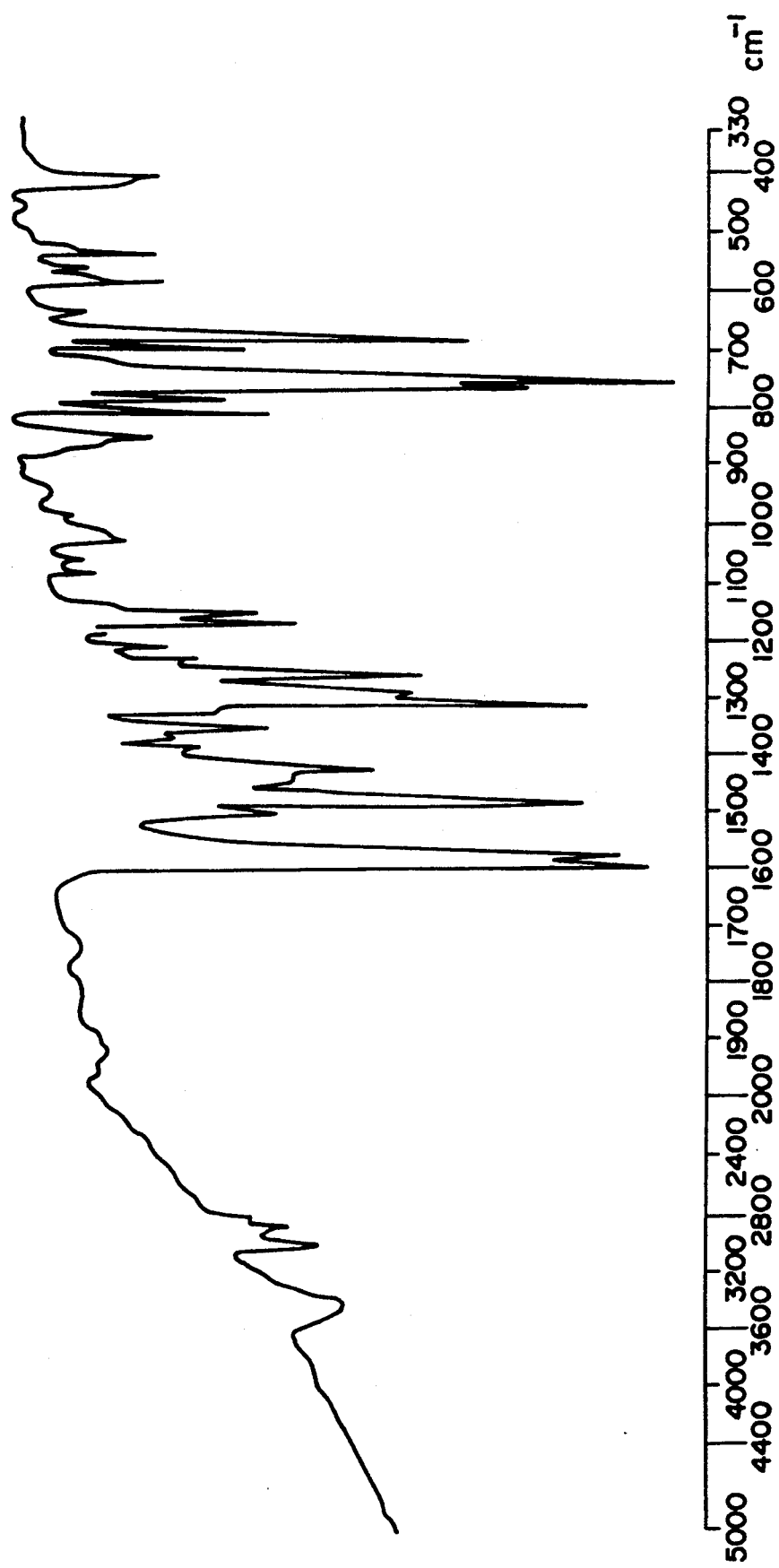
FIG. 2 is a chart of an infrared absorption spectrum, taken by the KBr tablet method, of the tertiary amine compound having a condensed polycyclic group according to the present invention prepared in Synthesis Example 4.

The infrared absorption spectrum chart taken by the KBr tablet method is shown in FIG. 2.

Synthesis Example 5

[Synthesis of Tertiary Amine Compound No. 14 in Table 1]

The synthesis procedure in Synthesis Example 1 was applied to obtain tertiary amine compound No. 14 in Table 1.

The melting point of the obtained compound, and the results of elementary analysis are shown in Table 2.

Synthesis Example 6

[Synthesis of Tertiary Amine Compound No. 9 in Table 1]

The synthesis procedure in Synthesis Example 1 was applied to obtain tertiary amine compound No. 9 in Table 1.

The melting point of the obtained compound, and the results of elementary analysis are shown in Table 2.

Synthesis Example 7

[Synthesis of Tertiary Amine Compound No. 10 in Table 1]

The synthesis procedure in Synthesis Example 1 was applied to obtain tertiary amine compound No. 10 in Table 1.

The melting point of the obtained compound, and the results of elementary analysis are shown in Table 2.

Figure 3:
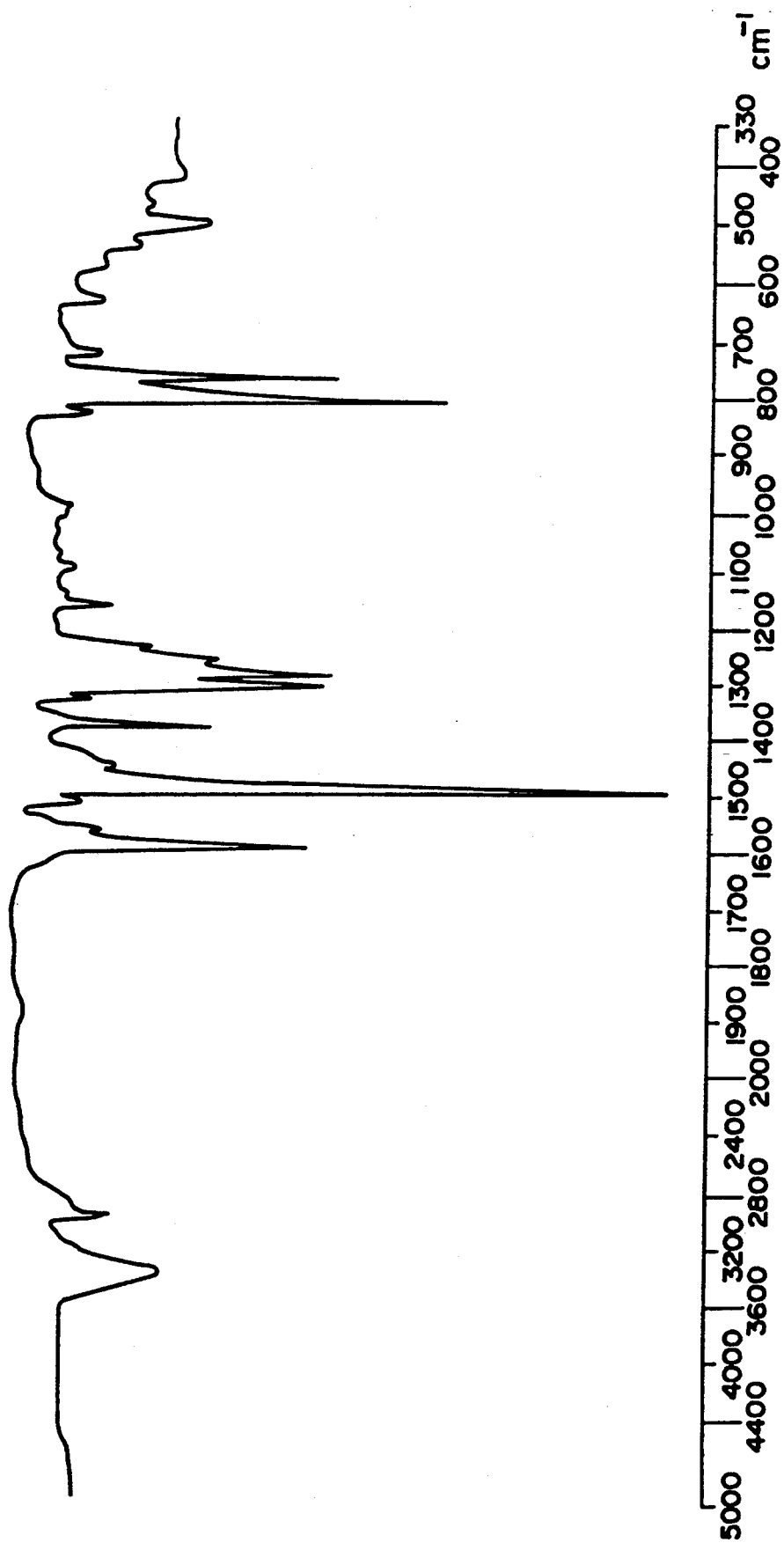
FIG. 3 is a chart of an infrared absorption spectrum, taken by the KBr tablet method, of the tertiary amine compound having a condensed polycyclic group according to the present invention prepared in Synthesis Example 7.

The infrared absorption spectrum chart taken by the KBr tablet method is shown in FIG. 3.

Synthesis Example 8

[Synthesis of Tertiary Amine Compound No. 8 in Table 1]

The synthesis procedure in Synthesis Example 1 was applied to obtain tertiary amine compound No. 8 in Table 1.

The melting point of the obtained compound, and the results of elementary analysis are shown in Table 2.

Figure 4:
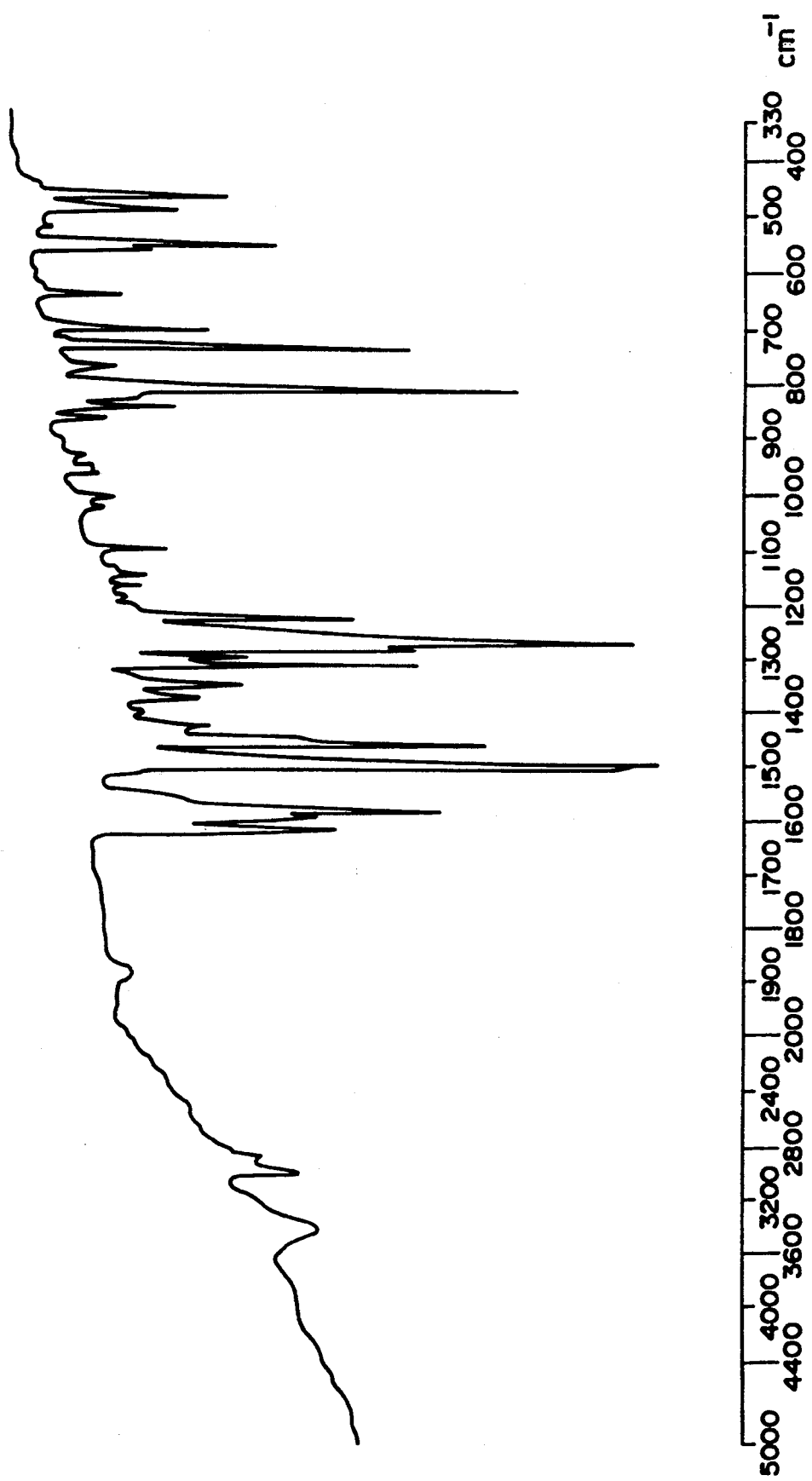
FIG. 4 is a chart of an infrared absorption spectrum, taken by the KBr tablet method, of the tertiary amine compound having a condensed polycyclic group according to the present invention prepared in Synthesis Example 8.

The infrared absorption spectrum chart taken by the KBr tablet method is shown in FIG. 4.

Synthesis Example 9

[Synthesis of Tertiary Amine Compound No. 12 in Table 1]

The synthesis procedure in Synthesis Example 1 was applied to obtain tertiary amine compound No. 12 in Table 1.

The melting point of the obtained compound, and the results of elementary analysis are shown in Table 2.

The infrared absorption spectrum chart taken by the KBr tablet method is shown in FIG. 5.

Synthesis Example 10

[Synthesis of Tertiary Amine Compound No. 13 in Table 1]

The synthesis procedure in Synthesis Example 1 was applied to obtain tertiary amine compound No. 13 in Table 1.

The the melting point of the obtained compound, and the results of elementary analysis are shown in Table 2.

Figure 6:
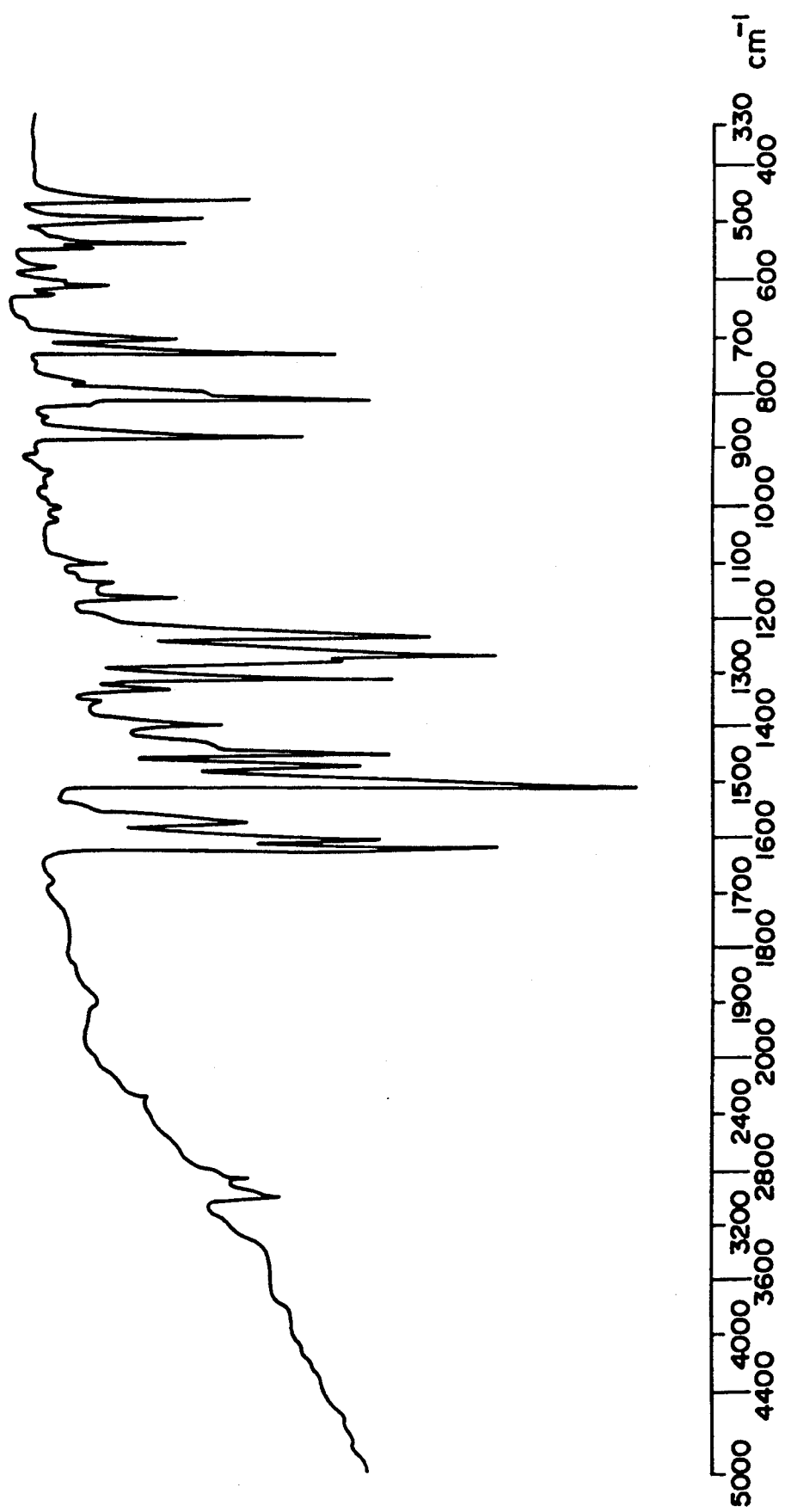
FIG. 6 is a chart of an infrared absorption spectrum, taken by the KBr tablet method, of the tertiary amine compound having a condensed polycyclic group according to the present invention prepared in Synthesis Example 10.

The infrared absorption spectrum chart taken by the KBr tablet method is shown in FIG. 6.

Synthesis Example 11

[Synthesis of Tertiary Amine Compound No. 16 in Table 1]

The synthesis procedure in Synthesis Example 1 was applied to obtain tertiary amine compound No. 16 in Table 1.

The melting point of the obtained compound, and the results of elementary analysis are shown in Table 2.

Synthesis Example 12

[Synthesis of Tertiary Amine Compound No. 15 in Table 1]

The synthesis procedure in Synthesis Example 1 was applied to obtain tertiary amine compound No. 15 in Table 1.

The melting point of the obtained compound, and the results of elementary analysis are shown in Table 2.

Synthesis Example 13

[Synthesis of Tertiary Amine Compound No. 17 in Table 1]

The synthesis procedure in Synthesis Example 1 was applied to obtain tertiary amine compound No. 17 in Table 1.

The melting point of the obtained compound, and the results of elementary analysis are shown in Table 2.

Figure 7:
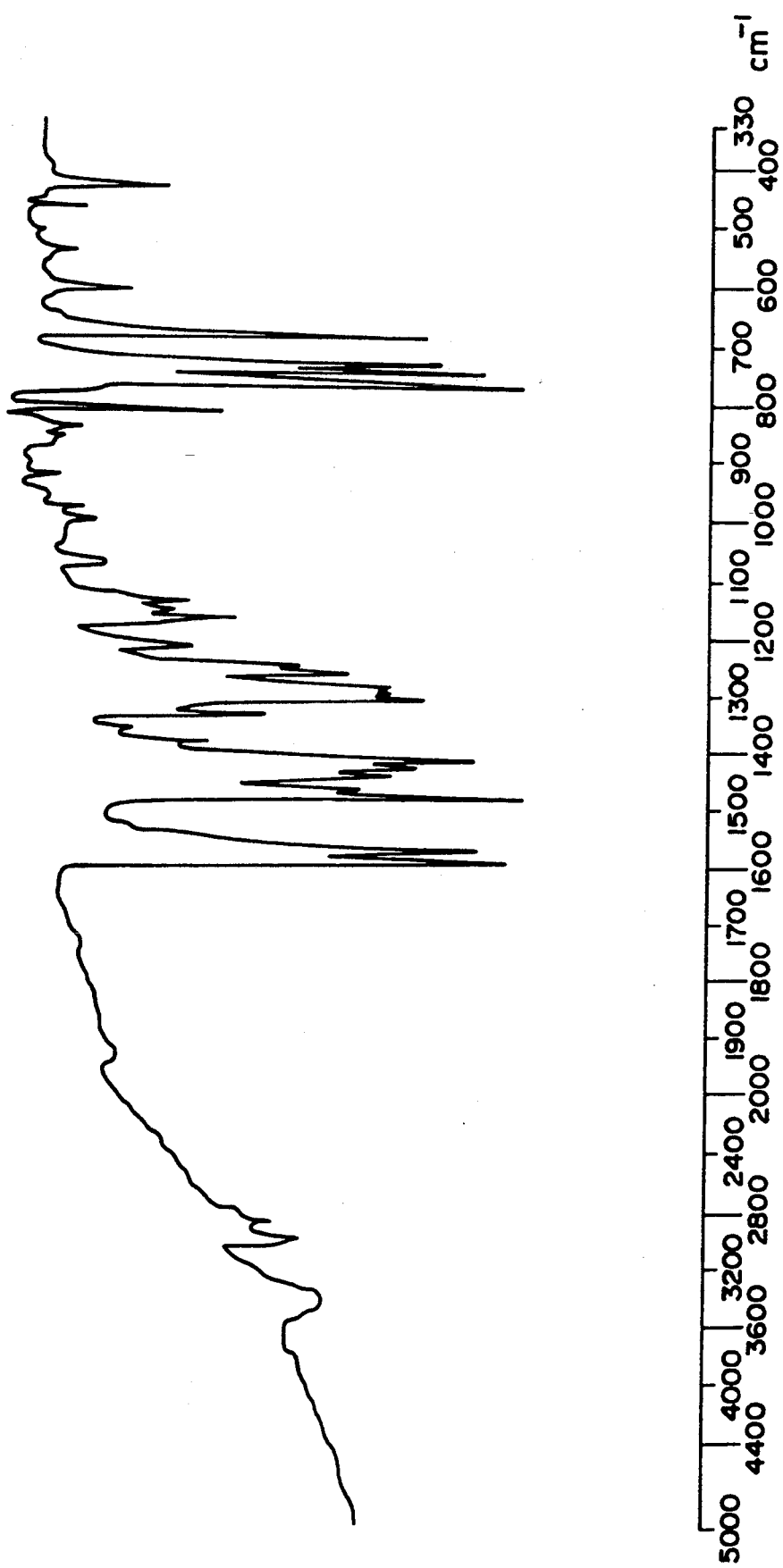
FIG. 7 is a chart of an infrared absorption spectrum, taken by the KBr tablet method, of the tertiary amine compound having a condensed polycyclic group according to the present invention prepared in Synthesis Example 13.

The infrared absorption spectrum chart taken by the KBr tablet method is shown in FIG. 7.

Synthesis Example 14

[Synthesis of Tertiary Amine Compound No. 11 in Table 1]

The synthesis procedure in Synthesis Example 1 was applied to obtain tertiary amine compound No. 11 in Table 1.

The melting point of the obtained compound, and the results of elementary analysis are shown in Table 2.

TABLE 2

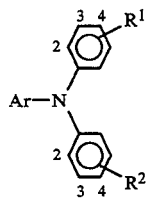

| Synthesis Example | Compound No. | Ar | $R^1$ | $R^2$ | Melting Point (°C.) | Elementary Analysis Found (Calculated) | | |
|---|---|---|---|---|---|---|---|---|
| | | | | | | % C | % H | % N |
| 2 | 2 | (pyrene) | 3-$CH_3$ | 3-$CH_3$ | 136.5–137.5 | 90.65 (90.64) | 5.57 (5.83) | 3.61 (3.53) |
| 3 | 5 | (chrysene) | 4-$CH_3$ | 4-$CH_3$ | 239.0–240.0 | 90.78 (90.74) | 6.03 (5.95) | 3.56 (3.31) |
| 4 | 6 | (chrysene) | 3-$CH_3$ | 3-$CH_3$ | 173.0–174.0 | 90.81 (90.74) | 5.98 (5.95) | 3.10 (3.31) |
| 5 | 14 | (methylfluorene) | 4-$CH_3$ | 4-$CH_3$ | 150.5–151.5 | 90.21 (90.04) | 6.14 (6.21) | 3.68 (3.75) |
| 6 | 9 | (methylnaphthalene) | 4-$CH_3$ | 4-$CH_3$ | Oily | 89.22 (89.11) | 6.60 (6.56) | 4.26 (4.33) |
| 7 | 10 | (methylnaphthalene) | 4-$C_6H_4CH_3$(P) | 4-$C_6H_4CH_3$(P) | 139.0–140.0 | 91.06 (90.90) | 6.05 (6.16) | 2.78 (2.95) |
| 8 | 8 | (methylnaphthalene) | 4-$CH_3$ | 4-$CH_3$ | 127.0–128.0 | 89.19 (89.11) | 6.32 (6.56) | 4.32 (4.33) |
| 9 | 12 | (methylanthracene) | 4-$CH_3$ | 4-$CH_3$ | 137.0–138.0 | 90.19 (90.03) | 6.04 (6.22) | 3.59 (3.75) |

TABLE 2-continued

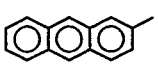

| Synthesis Example | Compound No. | Ar | R¹ | R² | Melting Point (°C.) | Elementary Analysis Found (Calculated) | | |
|---|---|---|---|---|---|---|---|---|
| | | | | | | % C | % H | % N |
| 10 | 13 | 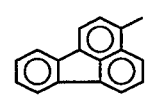 | 4-CH₃ | 4-CH₃ | 225.5–226.0 | 89.95 (90.03) | 6.24 (6.22) | 3.79 (3.75) |
| 11 | 16 |  | 4-CH₃ | 4-CH₃ | 196.5–197.5 | 90.60 (90.64) | 5.60 (5.83) | 3.70 (3.52) |
| 12 | 15 | 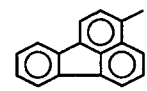 | 4-CH₃ | 4-CH₃ | 130.5–131.5 | 89.51 (89.36) | 6.61 (6.63) | 3.98 (4.01) |
| 13 | 17 | 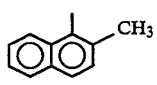 | 3-CH₃ | 3-CH₃ | 155.5–156.5 | 90.81 (90.64) | 5.85 (5.83) | 3.43 (3.52) |
| 14 | 11 |  | 4-CH₃ | 4-CH₃ | 94.0–95.5 | 88.79 (88.97) | 6.89 (6.88) | 4.13 (4.15) |

EXAMPLE 1

76 parts by weight of Diane Blue (C.I. Pigment Blue 25, C.I. 21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and ground in a ball mill pot. The thus prepared dispersion was coated on an aluminum surface of an aluminum-deposited polyester film by a doctor blade, and then dried at room temperature, so that a charge generation layer having a thickness of about 1 μm was formed on the aluminum-deposited polyester film.

2 parts by weight of tertiary amine compound No. 1 in Table 1 prepared in Synthesis Example 1, and 2 parts by weight of polycarbonate resin (Trademark "Panlite K-1300" made by Teijin Limited) were dissolved in 16 parts by weight of tetrahydrofuran to prepare a solution. The resulting solution was coated on the above formed charge generation layer by a doctor blade, and dried at 80° C. for 2 minutes and then at 120° C. for 5 minutes, so that a charge transport layer having a thickness of about 20 μm was formed on the charge generation layer. Thus a two-layered type electrophotographic photoconductor No. 1 according to the present invention was prepared.

EXAMPLES 2 to 45

The procedure for Example 1 was repeated except than the Diane Blue serving as a charge generating material and the tertiary amine compound No. 1 serving as a charge transporting material employed in Example 1 were replaced by the respective charge generating materials and charge transporting materials listed in the following Table 3, whereby two-layered type electrophotographic photoconductors No. 2 to No. 45 according to the present invention were prepared.

TABLE 3

| Photo-Conductor No. | Charge Generating Material | Charge Transporting Material (Tertiary Amine Compound No.) |
|---|---|---|
| 1 | [structure: bis-azo naphthol compound with OCH₃-substituted biphenyl central unit and phenyl-CONH / HNOC-phenyl end groups] | 1 |
| 2 | [structure: bis-azo naphthol compound with Cl-substituted biphenyl central unit and phenyl-CONH / HNOC-phenyl end groups] | 1 |
| 3 | [structure: bis-azo naphthol compound with stilbene-bis(azophenyl) central unit and 2,4-dimethylphenyl-CONH / HNOC-(2,4-dimethylphenyl) end groups] (hereinafter referred to as P-1) | 1 |

TABLE 3-continued
| Photo-Conductor No. | Charge Generating Material | Charge Transporting Material (Tertiary Amine Compound No.) |
|---|---|---|
| 4 | 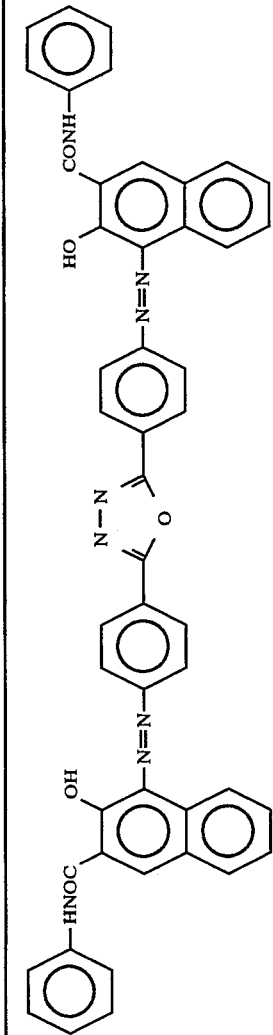 | 1 |
| 5 | 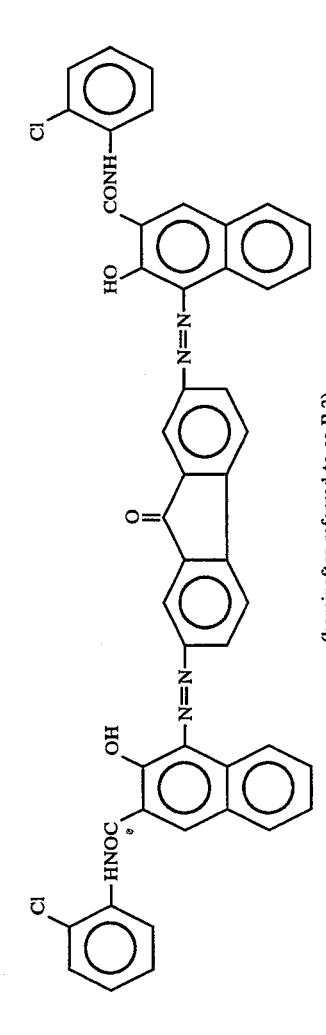 (hereinafter referred to as P-2) | 1 |
| 6 | 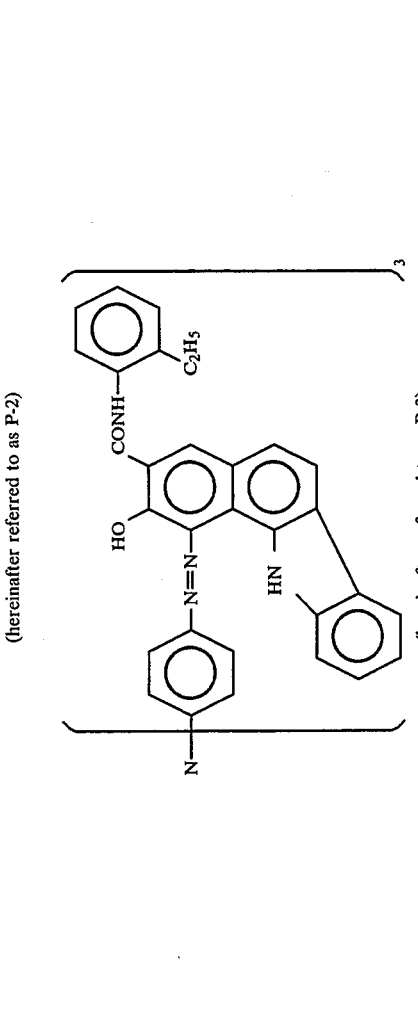 (hereinafter referred to as P-3) | 1 |
| 7 | β-type Copper Phthalocyanine | 1 |

TABLE 3-continued

| Photo-Conductor No. | Charge Generating Material | | Charge Transporting Material (Tertiary Amine Compound No.) |
|---|---|---|---|
| 8 | (structure: bis-azo naphthol with OCH₃ phenyl groups and CONH-phenyl amide) | | 1 |
| 9 | (structure: bis-azo naphthol with Cl phenyl groups and CONH-phenyl amide) | | 1 |
| 10 | | P-1 | 2 |
| 11 | | P-2 | 2 |
| 12 | | P-3 | 2 |
| 13 | | P-2 | 5 |
| 14 | | P-3 | 5 |
| 15 | | P-1 | 7 |
| 16 | | P-2 | 7 |
| 17 | | P-3 | 7 |
| 18 | | P-1 | 8 |
| 19 | | P-2 | 8 |
| 20 | | P-3 | 8 |
| 21 | | P-1 | 12 |
| 22 | | P-2 | 12 |
| 23 | | P-3 | 12 |
| 24 | | P-1 | 13 |
| 25 | | P-2 | 13 |
| 26 | | P-3 | 13 |
| 27 | | P-1 | 16 |
| 28 | | P-2 | 16 |
| 29 | | P-3 | 16 |
| 30 | | P-1 | 17 |
| 31 | | P-1 | |

TABLE 3-continued

| Photo-Conductor No. | Charge Generating Material | Charge Transporting Material (Tertiary Amine Compound No.) |
|---|---|---|
| 32 | P-2 | 17 |
| 33 | P-3 | 17 |
| 34 | P-1 | 10 |
| 35 | P-2 | 10 |
| 36 | P-3 | 10 |
| 37 | P-1 | 3 |
| 38 | P-2 | 3 |
| 39 | P-3 | 3 |
| 40 | P-1 | 4 |
| 41 | P-2 | 4 |
| 42 | P-3 | 4 |
| 43 | P-1 | 11 |
| 44 | P-2 | 11 |
| 45 | P-3 | 11 |

EXAMPLE 46

Selenium was vacuum-deposited on an aluminum plate having a thickness of about 300 μm which serves as an electroconductive substrate, so that a charge generation layer having a thickness of about 1 μm was formed on the aluminum plate.

2 parts by weight of tertiary amine compound No. 1 in Table 1, 3 parts by weight of polyester resin (Trademark "Polyester Adhesive 49000" made by Du Pont de Nemours, E.I. & Co.) were dissolved in 45 parts by weight of tetrahydrofuran. The resulting solution was coated on the above formed charge generation layer by a doctor blade, dried at room temperature, and then dried under reduced pressure, so that a charge transport layer having a thickness of about 10 μm was formed on the charge generation layer. Thus a two-layered type electrophotographic photoconductor No. 46 according to the present invention was prepared.

EXAMPLE 47

A perylene pigment having the following formula was vacuum-deposited on an aluminum plate having a thickness of about 300 μm, so that a charge generation layer having a thickness of about 0.6 μm was formed on the aluminum plate:

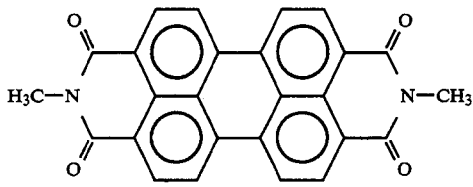

2 parts by weight of tertiary amine compound No. 1 in Table 1, 3 parts by weight of a polyester resin (Trademark "Polyester Adhesive 49000" made by Du Pont de Nemours, E.I. & Co.) were dissolved in 45 parts by weight of tetrahydrofuran. The resulting solution was coated on the above formed charge generation layer by a doctor blade, dried at room temperature, and then dried under reduced pressure, so that a charge transport layer having a thickness of about 10 μm was formed on the charge generation layer. Thus a two-layered type electrophotographic photoconductor No. 47 according to the present invention was prepared.

EXAMPLE 48

A mixture of 1 part by weight of the same Diane Blue as employed in Example 1 and 158 parts by weight of tetrahydrofuran was dispersed and ground in a ball mill pot to prepare a dispersion. To the thus prepared dispersion, 12 parts by weight of tertiary amine compound No. 1 in Table 1 and 18 parts by weight of polyester resin (Trademark "Polyester Adhesive 49000" made by Du Pont de Nemours, E.I. & Co.) were added to prepare a solution. The resulting solution was coated on an aluminum-deposited polyester film by a doctor blade, and dried at 100° C. for 30 minutes, so that a photoconductive layer having a thickness of about 16 μm was formed on the electroconductive support. Thus, an electrophotographic photoconductor No. 48 according to the present invention was prepared.

EXAMPLE 49

The solution for forming a charge transport layer, prepared in Example 1, was coated on an aluminum-deposited polyester film by a doctor blade, and dried at 80° C. for 2 minutes and then at 120° C. for 5 minutes, so that a charge transport layer having a thickness of about 20 μm was formed on the aluminum-deposited polyester film.

A mixture of 13.5 parts by weight of bisazo pigment (P-2), 5.4 parts by weight of polyvinyl butyral (Trademark "XYHL" made by Union Carbide Japan K.K.), 680 parts by weight of tetrahydrofuran and 1020 parts by weight of ethyl cellosolve was dispersed and ground in a ball mill pot. To this dispersion, 1700 parts by weight of ethyl cellosolve was further added to prepare a solution. The resulting was coated on the above formed charge transport layer by spray coating and dried at 100° C. for 10 minutes, so that a charge generation layer having a thickness of about 0.2 μm was formed on the charge transport layer.

A mixed solution of methanol and n-butanol containing a polyamide resin (Trademark "CM-8000" made by Toray Silicone Co., Ltd.) was coated on the above formed charge generation layer by spray coating and dried at 120° C. for 30 minutes, so that a protective layer having a thickness of about 0.5 μm was formed on the charge generation layer. Thus, a two-layered type electrophotographic photoconductor No. 49 according to the present invention was prepared.

Each of the above-prepared electrophotographic photoconductors No. 1 through No. 49 according to the present invention was charged negatively or positively in the dark under application of −6 kV or +6 kV of corona charge for 20 seconds, using a commercially available electrostatic copying sheet testing apparatus ("Paper Analyzer Model SP-428" made by Kawaguchi Electro Works Co., Ltd.). Then, each electrophotographic photoconductor was allowed to stand in the dark for 20 seconds without applying any charge thereto, and the surface potential Vpo (V) of the photoconductor was measured. The photoconductor was then illuminated by a tungsten lamp in such a manner that the illuminance on the illuminated surface of the photoconductor was 4.5 lux, and the exposure $E_{\frac{1}{2}}$ (lux·sec) required to reduce the initial surface potential Vpo (V) to ½ the initial surface potential Vpo (V) was measured. The results are shown in Table 4.

TABLE 4

| Photoconductor No. | Vpo (V) | $E_{\frac{1}{2}}$ (lux · sec) |
| --- | --- | --- |
| 1 | −1120 | 1.42 |
| 2 | −1060 | 1.25 |
| 3 | −1095 | 0.99 |
| 4 | −1250 | 2.20 |
| 5 | −1110 | 0.83 |
| 6 | −1025 | 0.54 |
| 7 | −1200 | 1.85 |
| 8 | −1230 | 1.52 |
| 9 | −1050 | 1.25 |
| 10 | −1105 | 0.99 |
| 11 | −1153 | 0.96 |
| 12 | −1133 | 0.70 |
| 13 | −1130 | 0.97 |
| 14 | −1170 | 0.94 |
| 15 | −1080 | 0.65 |
| 16 | −1140 | 0.99 |
| 17 | −1380 | 1.46 |
| 18 | −1181 | 1.11 |
| 19 | −1155 | 0.97 |
| 20 | −1204 | 0.96 |
| 21 | −1100 | 0.59 |
| 22 | −1110 | 1.01 |
| 23 | −1058 | 0.90 |
| 24 | −1026 | 0.68 |
| 25 | −1050 | 0.94 |

TABLE 4-continued

| Photoconductor No. | Vpo (V) | E₁/₂ (lux · sec) |
|---|---|---|
| 26 | −1120 | 0.88 |
| 27 | −1080 | 0.57 |
| 28 | −1180 | 0.98 |
| 29 | −1114 | 0.90 |
| 30 | −988 | 0.60 |
| 31 | −1120 | 0.96 |
| 32 | −1005 | 0.97 |
| 33 | −980 | 0.58 |
| 34 | −1095 | 0.98 |
| 35 | −1164 | 1.10 |
| 36 | −1120 | 0.61 |
| 37 | −1160 | 1.02 |
| 38 | −1375 | 1.13 |
| 39 | −1138 | 0.88 |
| 40 | −1085 | 0.98 |
| 41 | −1328 | 0.99 |
| 42 | −987 | 0.50 |
| 43 | −1250 | 1.15 |
| 44 | −1314 | 1.14 |
| 45 | −1120 | 0.76 |
| 46 | −940 | 2.10 |
| 47 | −1280 | 3.70 |
| 48 | +1290 | 1.70 |
| 49 | +1285 | 0.95 |

Each of the above-mentioned electrophotographic photoconductors according to the present invention was incorporated in a commercially available electrophotographic copying machine and charged negatively or positively. Then it was exposed to the light through an original to form a latent electrostatic image on the surface of the photoconductor. The thus formed latent electrostatic image was developed by a dry-type developer to a visible image. The resulting visible image was transferred to a sheet of plain paper and fixed thereon, so that a clear transferred image was formed. In the case where a wet-type developer was employed, a clear image was formed likewise.

Comparative Example 1

Example 1 was repeated except that the charge generating material used in Example 1 was replaced by a charge generating material P-2 shown in Table 3, and the tertiary amine compound No. 1 used as the charge transporting material in Example 1 was replaced by 4,4′,4″-trimethyltriphenyl amine, whereby a comparative electrophotographic photoconductor was prepared.

The electrophotographic photoconductor thus obtained was evaluated in the same manner as described above, and $V_{po}$ and $E_{\frac{1}{2}}$ were measured. In addition, the residual potential (Vr) 30 seconds after illumination was also measured.

The results are shown in Table 5 along with the data with respect to electrophotographic photoconductor No. 5 according to the present invention for comparison.

TABLE 5

| | $V_{po}$ | $E_{\frac{1}{2}}$ | Vr |
|---|---|---|---|
| Photoconductor No. 5 | −1110 | 0.83 | 0 |
| Comp. Photoconductor | −1287 | 1.24 | −129 |

The above data demonstrate that the electrophotographic photoconductor No. 5 according to the present invention has a higher photosensitivity, indicated by $E_{\frac{1}{2}}$, in comparison with the comparative photoconductor, and has no residual potential Vr.

The electrophotographic photoconductors according to the present invention are excellent in the photoconductive characteristics. Moreover, they are thermally and mechanically stable, and can be produced inexpensively.

What is claimed is:

1. A charge transporting material comprising a tertiary amine compound having a condensed polycyclic hydrocarbon group of formula (I):

wherein $A^1$ and $A^2$ each independently represent an unsubstituted or substituted alkyl group or aryl group, and Ar represents an unsubstituted or substituted condensed polycyclic hydrocarbon group selected from the group consisting of a pentalenyl group, an indenyl group, an azulenyl group, a heptalenyl group, a biphenylenyl group, an as-indacenyl group, an s-indacenyl group, an acenaphthenyl group, an acenaphthenyl group, a phenalenyl group, a phenanthryl group, a 1-anthryl group, a 2-anthryl group, a 2-naphthyl group, a fluoranthenyl group, an acephenanthrylenyl group, an aceanthrylenyl group, a triphenylenyl group, a pyrenyl group, a chrysenyl group and a naphthacenyl group.

2. The charge transporting material as claimed in claim 1, wherein said tertiary amine compound having a condensed polycyclic hydrocarbon group is a compound having formula (II):

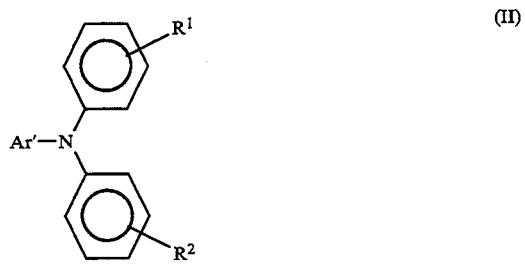

wherein Ar′ represents a condensed polycyclic hydrocarbon group having 18 or less carbon atoms, $R^1$ and $R^2$ each independently represent hydrogen, an alkyl group or alkoxyl group, which may have a substituent, or a phenyl group which may have a substituent.

3. A tertiary amine compound having formula (II):

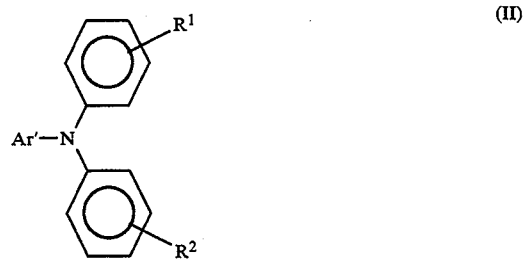

wherein Ar′ represents a condensed polycyclic hydrocarbon group having 18 or less carbon atoms, $R^1$ and $R^2$ each independently represent hydrogen, an alkyl group or alkoxyl group, which may have a substituent, or a phenyl group which may have a substituent.

4. The tertiary amine compound as claimed in claim 3, wherein said condensed polycyclic hydrocarbon group is selected from the group consisting of 2-naphthyl group, an acenaphthenyl group, an 1-anthryl group, an 2-anthryl group, a phenanthryl group, a chrysenyl group and a fluoranthenyl group.

5. The tertiary amine compound as claimed in claim 3, wherein said alkyl group represented by $R^1$ or $R^2$ is an alkyl group having 1 to 6 carbon atoms.

* * * * *

UNITED STATES PATENT AND TRADEMARK OFFICE
CERTIFICATE OF CORRECTION

PATENT NO. : 5,382,692
DATED : January 17, 1995
INVENTOR(S) : Tomoyuki SHIMADA et al It is certified that error appears in the above-indentified patent and that said Letters Patent is hereby corrected as shown below:

Column 1, line 48, "form" should read --from--.

Column 3, line 25, "advantageous" should read --advantages--.

Column 4, line 52, "n-buryl" should read --n-butyl--;

line 65, "a2-cyanoethoxy" should read --a 2-cyanoethoxy--.

Column 5, lines 17-18, "p-methylphenylthio group. (6) A group represented by",
should read --p-methylphenylthio group.

(6) A group represented by --.

line 20, "  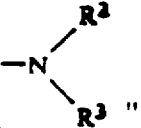 "

should read

-- 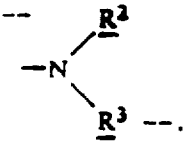 --.

UNITED STATES PATENT AND TRADEMARK OFFICE
CERTIFICATE OF CORRECTION

PATENT NO. : 5,382,692

DATED : January 17, 1995

INVENTOR(S) : Tomoyuki SHIMADA et al

It is certified that error appears in the above-indentified patent and that said Letters Patent is hereby corrected as shown below:

```
Column 6, line 29, "(V)" should read --(IV)--.
Column 10, line 17 "in" should --In--.
Column 12, line 3, "when" should read --When--;
          line 13, "it" should read --It--;
          line 44, "it" should read --It--;
          line 50, "it" should read --It--.
Column 14, line 3, "wich" should read --which--.
Column 16, line 55, "The the melting" should read
          --The melting--.

Column 32, lines 22-23, "an acenaphthenyl group, an acenaphthenyl
          group," should read --an acenaphthylenyl group, a
          pleiadenyl group, an acenaphthenyl group,--.

Column 32, line 26-27 delete "a pyrenyl group "
```

Signed and Sealed this

Seventeenth Day of September, 1996

*Attest:*

BRUCE LEHMAN

*Attesting Officer*  *Commissioner of Patents and Trademarks*